United States Patent [19]

Patel

[11] 3,981,312
[45] Sept. 21, 1976

[54] HAIR WAVING METHOD WITH A PREBONDER

[75] Inventor: Kanu I. Patel, Chatsworth, Calif.

[73] Assignee: Redken Laboratories, Inc., Van Nuys, Calif.

[22] Filed: July 3, 1975

[21] Appl. No.: 592,806

[52] U.S. Cl. .................. 132/7; 8/127.51; 424/70
[51] Int. Cl.² .......................................... A45D 8/00
[58] Field of Search ............... 132/7; 8/127.51; 424/70

[56] References Cited
UNITED STATES PATENTS

| | | | |
|---|---|---|---|
| 3,227,615 | 1/1966 | Korden | 132/7 |
| 3,266,994 | 8/1966 | Reiss | 8/127.51 |
| 3,849,548 | 11/1974 | Grand | 424/70 |
| 3,850,178 | 11/1974 | Schoenholz | 132/7 |

Primary Examiner—G.E. McNeill
Attorney, Agent, or Firm—Christie, Parker & Hale

[57] ABSTRACT

A process for cold waving hair includes the step of prebonding the hair by contacting it with both a water soluble polyvalent metal salt and a water soluble reactive polyamide-epichlorohydrin resin.

24 Claims, No Drawings

HAIR WAVING METHOD WITH A PREBONDER

BACKGROUND OF THE INVENTION

In the cold waving of hair it is common practice to soften or treat the hair with a reducing solution which permits shaping of the hair on a mandrel such as a curling rod, and then applying an oxidizing agent to the treated hair to neutralize the unreacted reducing agent and restore the strength of the hair. Unfortunately the oxidizing agent usually does not completely oxidize the reducing agent and completely restore the strength of the hair. Therefore, hair treated by conventional cold waving processes is left somewhat limp.

U.S. Pat. No. 3,266,994 describes a two step method where a water-soluble, non-toxic salt of a polyvalent metal is added to an aqueous solution of the oxidizing agent to increase the strength of treated hair.

U.S. Pat. No. 3,227,615 describes another method aimed at overcoming the problem of limp hair resulting from waving processes. This patent discloses a one step waving process whereby only a polyamide resin and a bisulfite salt are used to treat the hair.

Although these two processes marginally improve the quality of the treated hair, they do not give limp hair the strength, resiliency and body of healthy normal hair.

SUMMARY OF THE INVENTION

According to the present invention there is provided an unusually effective method for cold waving hair. Hair treated by this method exhibits the resiliency, strength, and body desired for normal healthy hair.

The method comprises the steps of reducing and oxidizing hair according to conventional techniques, and the step of prebonding the hair prior to oxidizing it. The hair is prebonded by contacting it with both an aqueous solution of at least one polyvalent metal salt, and an aqueous solution of at least one water-soluble reactive polyamide-epichlorohydrin resin. Although the prebonding can be effected by first contacting the hair with the salt and then by the resin, or vice versa, it is preferred that the salt and resin be used together.

The resin used in the prebonding solution is a water soluble, reactive, polyamide-epichlorohydrin resin. The preferred resins are those formed by the reaction of epichlorohydrin with the polymer formed by the reaction of adipic acid and diethylene triamine. The preferred polyvalent metal salt is magnesium sulfate.

Depending on the end use application and the degree set desired, the composition independently or in combination may contain from about 1 to about 4% by weight resin, and polyvalent salt in an amount of from about 20% by weight to solution saturation. The pH of the prebonding solution is from about 3 to about 8, and preferably from about 4 to about 5. In the case of magnesium sulfate, saturation occurs at about 30% by weight in a solution of 4.5 pH.

The prebonding solution of this invention can be applied to the hair as an aerosol spray using conventional propellants, as a non-aerosol spray from a container using a plunger type pump, or preferably as a lotion solution.

It has been found that this combination of the polyvalent metal salt and the water soluble, reactive polyamide-epichlorohydrin resin act synergistically to give treated limp hair the resiliency, strength, and body of normal hair.

DETAILED DESCRIPTION OF THE INVENTION

The present invention pertains to a three stage cold waving system for hair, comprising contacting the hair with a reducing solution, a prebonding solution, and finally an oxidizing solution.

More particularly, the hair is, after reducing, prebonded by contacting it with a water soluble, non-toxic polyvalent metal salt and a water soluble reactive, polyamide-epichlorohydrin resin alone or in combination in aqueous prebonding solution.

By a "polyvalent metal salt" there is meant non-toxic water soluble salts where the metal cation has a valence greater than one.

Suitable polyvalent metal salts include calcium chloride, calcium acetate, aluminum sulfate, magnesium sulfate, and the like. The presently preferred salt is magnesium sulfate.

As used herein by the term "water soluble, reactive polyamide-epichlorohydrin resins", there is meant resins derived from the reaction of epichlorohydrin with a polyamide polymer obtained by reaction of a polyalkylene polyamine with saturated dicarboxylic acid. The resins have the general formula:

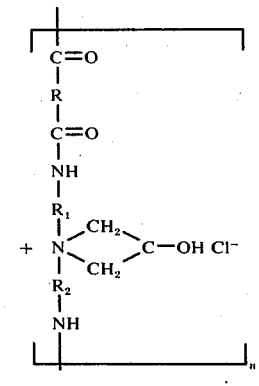

wherein R is an alkyl group containing from 1 to about 6 carbon atoms, $R_1$ and $R_2$ are independently alkyl groups containing at least 2 and preferably from about 2 to about 4 carbon atoms, and $n$ is the number of repeating units in the molecule. Each alkyl group may be straight or a branched chain.

The presently preferred water soluble reactive polyamide-epichlorohydrin resins are formed by the reaction of epichlorohydrin with the reaction product of diethylene triamine and adipic acid. Mixtures of resins may be used.

In the resin, the chlorine may be replaced by other anions, such as phosphate, which do not alter the reactive nature of the cationic thermosetting resins.

The preparation of the water soluble, reactive polyamide-epichlorohydrin resins are described in detail in U.S. Pat. No. 3,227,615 issued Jan. 4, 1966, incorporated herein by reference.

Quite surprisingly, when hair is contacted with both the polyvalent metal salt and the water soluble, reactive polyamide-epichlorohydrin resin before it is oxidized during a waving treatment, the treated hair exhibits the resiliency, strength, and body of normal hair. Typically, when fine limp hair is permanently waved with conventional systems the hair normally retains its wave for only about two to four weeks. When this same hair is treated with the prebonding solution in combination with conventional waving systems, the hair may retain its wave from 8 to 12 weeks.

While not bound by theory, I belive that this unexpected result occurs because the polyvalent salt increases the salt linkages in the hair, and the water soluble, reactive polyamide-epichlorohydrin resin reacts with the sulfhydryl groups of the hair. Because of this increase in total bonds, there is a net increase in strength and elasticity of the hair. Therefore the hair has more resiliency, body, and strength, and appears to be less limp.

In the practice of this invention, a prebonding solution containing from about 1 to about 4% by water weight of the reactive, water soluble epichlorohydrin-polyamide resin is used, preferably about 2% by weight resin. As part of the same or a different aqueous solution, from about 20% by weight to saturation of the polyvalent metal salt is also applied as part of the prebonding treatment. The pH of the prebonding solution employed may vary widely and range from a pH of about 3 to about 8. Preferably the solution is acidic with a pH from about 4 to about 5.

Although it is preferred to employ an aqueous prebonding solution containing both the polyvalent metal salt and the water soluble, reactive polyamide-epichlorohydrin resin, the same results can be obtained by using the salt and resin in sequentially applied solutions. Hair can be first contacted with a solution containing only the salt, and then with a solution containing the resin, or vice versa. However, the same results are not obtained if only the salt or only the resin is used, as is amply demonstrated by the example and controls below.

In addition to a polyvalent metal salt and a water soluble, reactive polyamide-ephichlorohydrin resin, the prebonding solution(s) may contain other components such as wetting agents, surfactants, perfumes, and the like.

This process of reducing, prebonding and then oxidizing hair is utile with any conventional waving process, including both acidic and alkaline processes. However, it is preferred that the prebonding solution be used with the method and acidic solutions described in U.S. Pat. No. 3,847,165 issued to myself and one other. Thus it is preferred that the hair be first contacted with a two stage reducing solution consisting of urea, methyl urea, ethyl urea, or a mixture thereof, as all or part of a first stage. The first stage is dissolved in a second stage to provide a resulting aqueous solution which is from 1 to 4 molar in the urea compound, 0.8 to 1.4 molar in a water soluble thiol such as ammonium thioglycolate, 0 to 0.6 molar in a bicarbonate compound such as ammonium bicarbonate, 0 to 0.007 molar in borax, and from 2 to 5% by weight in a water soluble protein, the solution having a pH between 6 and 6.8. A preferred aqueous reducing solution consists of 3.0 moles/liter urea, 1.3 moles/liter ammonium thioglycolate, 1.0 grams sodium bicarbonate per 100 grams of solution, 0.25 grams borax per 100 grams of solution, 2.0% by weight of solution of protein, and a pH of 6.5.

The hair is then rinsed with tepid water to remove the reducing solution. Following treatment with the reducing waving solution, the hair is prebonded with the solutions of this invention. The hair is again rinsed with tepid water. There is then applied acidic protein bonding or neutralizing solutions (pH about 6.1) which are typically an aqucous solution containing oxidizing agents such as hydrogen peroxide, potassium bromate, alkali metal perborates, such as sodium and potassium perborate, and the like, as well as mixtures thereof, which neutralize the redox effect of the reforming solution. That is to curb reduction of the hair while the reforming solution is oxidized. This also constitutes a rebonding operation to assure rebonding of the hair ends. The hair is then styled.

A preferred means for supplying the prebonding solution(s) to customers is in fit form, where the kit contains packages of reducing solution, prebonding solution(s), and oxidizing solution. The packages are those functional for the solution they contain. In the instance of lotions, they are typically capped plastic bottles. Spray bottles or the like may also be used.

The advantages of this invention are better understood with reference to the following comparative study illustrating the benefit of using the compositions of this invention.

CONTROLS AND EXAMPLE

A swatch of strands of hair having an average cross sectional area of about 1500 square microns was divided into five subswatches, Controls A, B, C and D, and the Example. Table I summarizes the treatment applied to each subswatch.

Control A was untreated.

Controls B, C and D and the Example were each wound on a ⅜ inch diameter spiral shaped mandrel to impart curl, reduced by immersion in a reducing solution of 12% by weight of ammonium thioglycolate for 20 minutes, capped with a plastic bag, dried by exposure to hot air maintained at 120°F, water rinsed in tepid water (80°–100°F) for 3 to 5 minutes, and then towel blotted.

Control B was oxidized by immersion for 5 minutes in a 10% solution of sodium bromate, rinsed for 3 to 5 minutes in tepid water, and then dried.

Control C was treated in the same manner as Sample B, except that the subswatch was immersed in a room temperature aqueous solution containing 2.0% by weight of a reactive polyamide-epichlorohydrin resin known as DELSETTE 101, manufactured and sold by Hercules Powder Company, before it was oxidized.

Control D was treated in the same manner as Control B except that the hair sample was immersed in a room temperature 30% by weight aqueous solution of magnesium sulfate for 3 minutes prior to oxidation.

The Example was treated in accordance with this invention. It was treated in the same way as Control B except that prior to the oxidation step, it was contacted with a room temperature aqueous solution of 4.5 pH containing 30% by weight magnesium sulfate and 2.0% by weight of the reactive, polyamide-epichlorohydrin resin (DELSETTE 101).

Tensile properties of individual hairs randomly selected from each subswatch were determined in a stress-strain tester which draws a 0.75 inch length of clamped hair at an elongation rate of 1.5% per second. Force in grams at 2% elongation and elongation at break point were measured using a Stratham transducer and were recorded on a Hewlett-Packard x-y recorder.

The physical properties of the untreated and treated hair samples are shown in Table II.

Since the original untreated hair had an original average cross sectional area of about 1500 square microns and would extend over 45% before break, it was categorized as "fine limp". Average healthy hair has an elongation at break of 35 to 45%, and ideally, 38 to 42%.

The hair of the treated controls had about the same low elasticity and high elongation at break as the untreated hair. The prebond treatment of Control C improved elasticity as compared to Controls A and B, but worsened elongation. The prebond treatment of Control D improved elasticity, but had an adverse effect on elongation.

The prebond treatment of the Example using the composition of the invention resulted in the most significant improvement in elasticity. It also reduced elongation at break point to within the range for normal hair. These results show the surprising synergistic effect of a prebonding treatment utilizing both a water soluble polyvalent metal salt and a water soluble, reactive polyamide-epichlorohydrin resin.

TABLE I

| Control/Example | Reduced | Prebonded | Oxidized |
| --- | --- | --- | --- |
| Control A | No | No | No |
| Control B | Yes | No | Yes |
| Control C | Yes | With resin | Yes |
| Control D | Yes | With salt | Yes |
| Example | Yes | With resin & salt | Yes |

TABLE II

| Example or Control | Elasticity gm/$\mu^2$ (at 2% Elongation) | % Change in Elasticity | % Elongation at Break Point | % Change in Elongation at Break Point | % Reduction in Diameter as Result of Treatment |
| --- | --- | --- | --- | --- | --- |
| Control A | 0.01720 | 0.00 | 48.8 | 0.00 | 0.00 |
| Control B | 0.01777 | 3.31 | 45.0 | −7.79 | 5.64 |
| Control C | 0.01758 | 2.21 | 48.7 | −0.20 | 3.32 |
| Control D | 0.01803 | 4.83 | 51.0 | +4.50 | — |
| Example | 0.01921 | 11.69 | 41.5 | −14.96 | 12.35 |

What is claimed is:

1. In a process for waving hair which includes the steps of contacting the hair with a reducing agent to reduce the hair followed by contacting the hair with an oxidizing agent to reconstitute the hair, the improvement comprising the step of prebonding the hair prior to contact with the oxidizing agent by contact with at least one polyvalent metal salt in an aqueous solution and at least one water soluble reactive polyamide-epichlorohydrin resin in an aqueous solution.

2. A process as claimed in claim 1 wherein the step of prebonding comprises contacting the hair with an aqueous solution containing at least one polyvalent metal salt and at least one reactive water soluble polyamide-epichlorohydrin resin.

3. A process as claimed in claim 1 wherein the step of prebonding the hair comprises contacting the hair, after reduction, with separate applications of an aqueous solution of at least one polyvalent metal salt and an aqueous solution of at least one water soluble, reactive polyamide-epichlorohydrin resin.

4. A process as claimed in claim 1 wherein the step of prebonding comprises contacting the hair with an aqueous solution containing the water soluble, reactive polyamide-epichlorohydrin resin in an amount of from about 1.0 to about 4.0% by weight based on the total weight of the solution.

5. A process as claimed in claim 4 wherein the step of prebonding comprises contacting the hair with an aqueous solution containing the polyvalent metal salt in an amount of from about 20% based on the total weight of the solution to solution saturation.

6. A process as claimed in claim 1 wherein the step of prebonding comprises contacting the hair with an aqueous solution containing the polyvalent metal salt in an amount of from about 20% based on the total weight of the solution to solution saturation.

7. A process as claimed in claim 1 wherein the polyvalent metal salt is magnesium sulfate.

8. A process as claimed in claim 1 wherein the water soluble, reactive polyamide-epichlorohydrin resin is the resin formed by the reaction of epichlorohydrin with the reaction product of diethylene triamine and adipic acid.

9. A prebonding composition for improving the body of hair in a waving process which comprises an aqueous solution of at least one polyvalent metal salt and a reactive, water soluble polyamide-epichlorohydrin resin.

10. A composition of claim 9 in which the water soluble, reactive polyamide-epichlorohydrin resin is present in an amount from about 1.0 to about 4.0% by weight based on the total weight of the solution.

11. A composition of claim 10 in which the polyvalent metal salt is present in an amount from about 20% based on the total weight of the solution to solution saturation.

12. A composition of claim 9 in which the polyvalent metal salt is present in an amount from about 20% based on the total weight of the solution to solution saturation.

13. The prebonding composition as claimed in claim 9 wherein the polyvalent metal salt is magnesium sulfate.

14. The prebonding composition as claimed in claim 9 wherein the water soluble, reactive polyamide-epichlorohydrin resin is the resin formed by the reaction of epichlorohydrin with the reaction product of diethylene triamine and adipic acid.

15. A kit for waving of hair comprising:
 a. a packaged reducing solution for the hair;
 b. a packaged aqueous prebonding solution of at least one polyvalent metal salt and a reactive water soluble polyamide-epichlorohydrin resin; and
 c. a packaged oxidizing solution for the hair.

16. A kit as claimed in claim 15 wherein the prebonding solution contains the water soluble, reactive polyamide-epichlorohydrin resin in an amount from about 1.0 to about 4.0% by weight based on the total weight of the solution.

17. A kit as claimed in claim 16 wherein the polyvalent metal salt is present in an amount from about 20% based on the total weight of the solution to solution saturation.

18. A kit as claimed in claim 15 wherein the prebonding solution contains the polyvalent metal salt in an amount from about 20% based on the total weight of the solution to solution saturation.

19. A kit as claimed in claim 15 wherein the polyvalent metal salt is magnesium sulfate.

20. A kit as claimed in claim 15 wherein the water soluble, reactive polyamide-epichlorohydrin resin is the resin formed by the reaction of epichlorohydrin with the reaction product of diethylene triamine and adipic acid.

21. A method for waving hair comprising the steps of:
   a. reducing the hair by contacting the hair with an aqueous reducing solution comprising:
      i. a first stage comprising a urea compound selected from the group consisting of urea, methyl urea, ethyl urea and mixtures thereof; and
      ii. a second stage comprising water, a water soluble thiol and a water soluble protein, where the first stage is added to the second stage alone or with water forming a net solution having a pH between about 6.0 and about 6.8, the net solution having a urea compound concentration of from about 1 to about 4 molar, a water soluble thiol concentration of from about 0.8 to about 1.4 molar and a water soluble protein content of from about 2 to about 5 percent by weight based on the total weight of the net solution;
   b. prebonding the hair by contact with at least one polyvalent metal salt in an aqueous solution and at least one water soluble, reactive polyamide-epichlorohydrin resin in an aqueous solution; and
   c. oxidizing the hair by contacting the hair with an oxidizing solution.

22. A method as claimed in claim 21 wherein the step of prebonding comprises contacting the hair with an aqueous solution containing the water soluble, reactive polyamide-epichlorohydrin resin in an amount of from about 1.0 to about 4.0% by weight based on the total weight of the solution.

23. A method as claimed in claim 22 wherein the step of prebonding comprises contacting the hair with an aqueous solution containing the polyvalent metal salt in an amount of from about 20% based on the total weight of the solution to solution saturation.

24. A method as claimed in claim 21 wherein the step of prebonding comprises contacting the hair with an aqueous solution containing the polyvalent metal salt in an amount of from about 20% based on the total weight of the solution to solution saturation.

* * * * *